(12) United States Patent
Williams

(10) Patent No.: US 10,265,110 B2
(45) Date of Patent: Apr. 23, 2019

(54) PEDICLE SCREW WITH RAISED ROOT

(71) Applicant: Alphatec Spine, Inc., Carlsbad, CA (US)

(72) Inventor: Lawrence Williams, Valley Center, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 164 days.

(21) Appl. No.: 15/297,860

(22) Filed: Oct. 19, 2016

(65) Prior Publication Data

US 2017/0105778 A1    Apr. 20, 2017

Related U.S. Application Data

(60) Provisional application No. 62/243,391, filed on Oct. 19, 2015.

(51) Int. Cl.
| | |
|---|---|
| A61B 17/86 | (2006.01) |
| A61B 17/00 | (2006.01) |
| A61B 17/70 | (2006.01) |

(52) U.S. Cl.
CPC .......... *A61B 17/863* (2013.01); *A61B 17/866* (2013.01); *A61B 17/8615* (2013.01); *A61B 17/8625* (2013.01); *A61B 17/8635* (2013.01); *A61B 17/7035* (2013.01); *A61B 2017/0088* (2013.01); *A61B 2017/00526* (2013.01); *A61B 2017/8655* (2013.01)

(58) Field of Classification Search
CPC ............. F16B 25/0068; F16B 25/0026; A61B 17/863; A61B 17/8615; A61B 17/8635; A61B 17/866; A61B 2017/00526; A61B 2017/0088; A61B 2017/8655

USPC .......................... 411/311, 412; 606/300–321
See application file for complete search history.

(56) References Cited

U.S. PATENT DOCUMENTS

| | | | | |
|---|---|---|---|---|
| 2,520,232 | A | * | 8/1950 | Bereza ................ F16B 25/0015 411/17 |
| 2,788,045 | A | * | 4/1957 | Rosan ..................... F16B 39/32 285/390 |
| RE27,678 | E | * | 6/1973 | Orlomoski .............. F16B 39/30 411/311 |
| 5,209,753 | A | | 5/1993 | Biedermann et al. |
| 5,336,015 | A | * | 8/1994 | Stewart ..................... H05B 7/14 314/60 |
| 5,478,342 | A | * | 12/1995 | Kohrs ................ A61B 17/8685 606/310 |
| 5,713,904 | A | | 2/1998 | Enrico et al. |
| 5,743,914 | A | * | 4/1998 | Skiba ................. A61B 17/8625 411/412 |
| 5,814,046 | A | | 9/1998 | Hopf |

(Continued)

*Primary Examiner* — Zade Coley
*Assistant Examiner* — Jessica Weiss
(74) *Attorney, Agent, or Firm* — Honigman LLP

(57) ABSTRACT

A self-locking screw with a raised root is provided. The self-locking screw has a head, a distal end, and a shaft extending between the head and the distal end. The shaft includes a thread with a plurality of turns so as to define a root, the raised root extending over the root for at least a subset of the plurality of turns proximal to the head. The raised root is removably attached to the root and detaches from the root when the self-locking screw is screwed into a substrate such that the detached raised root binds between the self-locking screw and the substrate and/or becomes embedded within the substrate.

19 Claims, 6 Drawing Sheets

(56) References Cited

U.S. PATENT DOCUMENTS

| | | | | |
|---|---|---|---|---|
| 5,957,646 | A * | 9/1999 | Giannuzzi | F16B 25/00 |
| | | | | 411/311 |
| 6,514,026 | B1 * | 2/2003 | Gerhard | C21D 9/0093 |
| | | | | 411/311 |
| 6,668,688 | B2 | 12/2003 | Zhao et al. | |
| 7,309,199 | B2 * | 12/2007 | Ayrle | C04B 28/24 |
| | | | | 411/258 |
| 7,445,627 | B2 | 11/2008 | Hawkes et al. | |
| 2004/0258502 | A1 * | 12/2004 | Unsworth | F16B 25/0031 |
| | | | | 411/412 |
| 2005/0084360 | A1 * | 4/2005 | Panasik | F16B 13/002 |
| | | | | 411/44 |
| 2006/0165506 | A1 * | 7/2006 | Panasik | F16B 13/002 |
| | | | | 411/30 |
| 2006/0241776 | A1 * | 10/2006 | Brown | A61B 17/0401 |
| | | | | 623/20.16 |
| 2008/0219801 | A1 * | 9/2008 | Toenjes | F16B 25/0015 |
| | | | | 411/413 |
| 2008/0232926 | A1 * | 9/2008 | Hsu | F16B 25/0026 |
| | | | | 411/412 |
| 2009/0003966 | A1 * | 1/2009 | Hsu | F16B 15/06 |
| | | | | 411/394 |
| 2009/0131992 | A1 | 5/2009 | Greenhalgh et al. | |
| 2009/0192552 | A1 | 7/2009 | Andersen et al. | |
| 2012/0116465 | A1 * | 5/2012 | Elahinia | A61B 17/8625 |
| | | | | 606/310 |
| 2012/0257945 | A1 * | 10/2012 | Phua | F16B 25/0047 |
| | | | | 411/311 |
| 2016/0157908 | A1 * | 6/2016 | Cawley | B22F 3/1055 |
| | | | | 606/301 |

\* cited by examiner

PEDICLE SCREW WITH RAISED ROOT

CROSS-REFERENCE TO RELATED APPLICATIONS

This Application claims the benefit of U.S. Provisional Application 62/243,391 filed on Oct. 19, 2015. The entire contents of these applications are incorporated herein by reference in their entirety.

FIELD OF THE INVENTION

The instant application is directed to a screw, and in particular, to a self-locking screw having a raised root for binding the self-locking screw in a substrate material.

BACKGROUND OF THE INVENTION

Screws for use in medical operations are known. Such screws typically have a thread with a plurality of turns so as to define a root. The screw is rotated with a force applied in a proximal to distal direction of the screw (screwed) into a substrate such as a bone, implant, etc. It is desirable the screw remain in a secured position once it has been fully installed (screwed) into the substrate. Accordingly, a need exist for an improved screw with an increase in binding or anchoring strength between the screw and the substrate.

SUMMARY OF THE INVENTION

A self-locking screw for binding to a substrate of a surgical site is provided. The self-locking screw includes a head, a distal portion, and a shaft extending between the head and the distal portion. The shaft includes a thread with a plurality of turns so as to define a root. A raised root extends over the root and a portion of the raised root. In one embodiment a raised root is removably attached to the root along at least a subset of the plurality of turns proximal to the head. The raised root detaches from the root so as to bind between the shaft of the self-locking screw and a substrate when the subset of the plurality of turns proximal to the head is screwed into the substrate.

In embodiments, an interface is present between the root and the raised root and the raised root detaches from the root at the interface so as to facilitate radial displacement of the raised root and binding of the raised root between the shaft of the self-locking screw and the substrate. The raised root may be formed from the same material as the root, or in the alternative, the raised root may be formed from a different material than the root. The substrate may be a bone substrate and the raised root may detach from the root so as to embed within the bone substrate when the self-locking screw is screwed into the bone substrate and the raised root comes into sliding contact therewith. The substrate may be an implant substrate and the raised root may detach from the root so as to bind between the shaft of the self-locking screw and the implant substrate when the self-locking screw is screwed into the implant substrate and the raised root comes into sliding contact therewith.

In embodiments, the self-locking screw is screwed into a bone substrate and an implant substrate, and the raised root is configured to remain fixed or attached to the root when the raised root comes into sliding contact with the bone substrate, but the raised root detaches from the root and binds between the shaft of the self-locking screw and the implant substrate when the raised root comes into sliding contact with the implant substrate.

A method for securing a self-locking screw during a surgical procedure is also provided. The method includes screwing a self-locking screw into a surgical site substrate, the self-locking screw comprising a head, a distal end, and a shaft extending between the head and the distal end. The shaft includes a thread with a plurality of turns so as to define a root and a raised root extends over the root. A portion of the raised root is removably attached along at least a subset of the plurality of turns proximal the head and the raised root detaches from the root so as to bind between the shaft of the self-locking screw and a substrate when the subset of the plurality of turns proximal the head is screwed into the substrate and the raised root comes into sliding contact therewith. The self-locking screw may have an interface between the root and the raised root such that the raised root detaches from the root at the interface, i.e., the interface facilitates radial displacement of the raised root to bind between the shaft of the self-locking screw and the substrate. The self-locking screw may be screwed into a bone substrate and the raised root detached from the root becomes embedded within the bone substrate when the shaft is screwed into the bone substrate and the raised root comes into sliding contact therewith. The self-locking screw may be screwed into a bone substrate and an implant substrate, and the raised root fails to detach from the root, i.e., the raised root remains attached to the root, when the shaft is screwed into the bone substrate and the raised root comes into sliding contact with the bone substrate. However, the raised root does detach from the root and binds between the thread and the implant substrate when the raised root comes into sliding contact with the implant substrate.

Additional features and advantages of the self-locking screw described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments that are intended to provide an overview or framework for understanding the nature and character of the claimed subject matter. The accompanying drawings are included to provide a further understanding of the various embodiments, and are incorporated into and constitute a part of this application. The drawings illustrate the various embodiments described herein, and together with the description serve to explain the principles and operations of the claimed subject matter.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings where like structure is indicated with like reference numerals and in which:

DETAILED DESCRIPTION OF THE INVENTION

A self-locking screw with increased binding or anchoring strength is provided. The self-locking screw has a head (also referred to as a "proximal end" herein), a distal portion, and a shaft extending between the head and the distal portion. The shaft comprises a thread with a plurality of turns so as to define a root. A raised root extends over the root and a portion of the raised root is removably attached to the root along at least a subset of the plurality of turns proximal the head. The raised root detaches from the root when the raised root comes into sliding contact with a substrate so as to bind between the shaft and the substrate which the self-locking screw has been screwed into.

Figure 1:
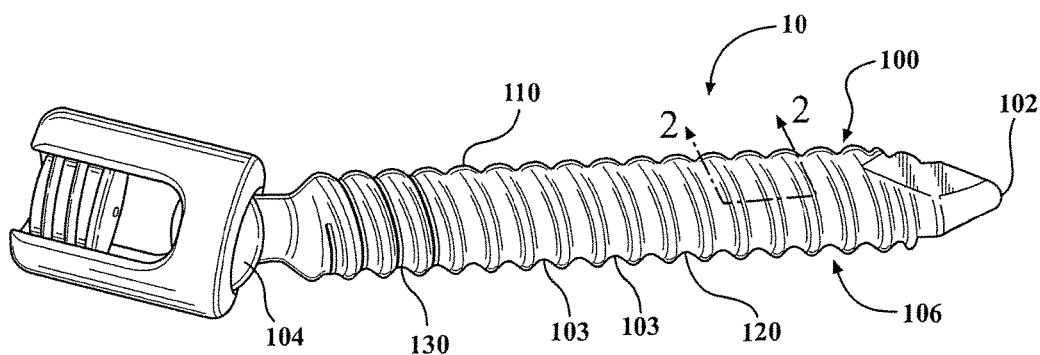
FIG. 1 schematically depicts a self-locking screw according to one or more embodiments shown and described herein.
Figure 2:
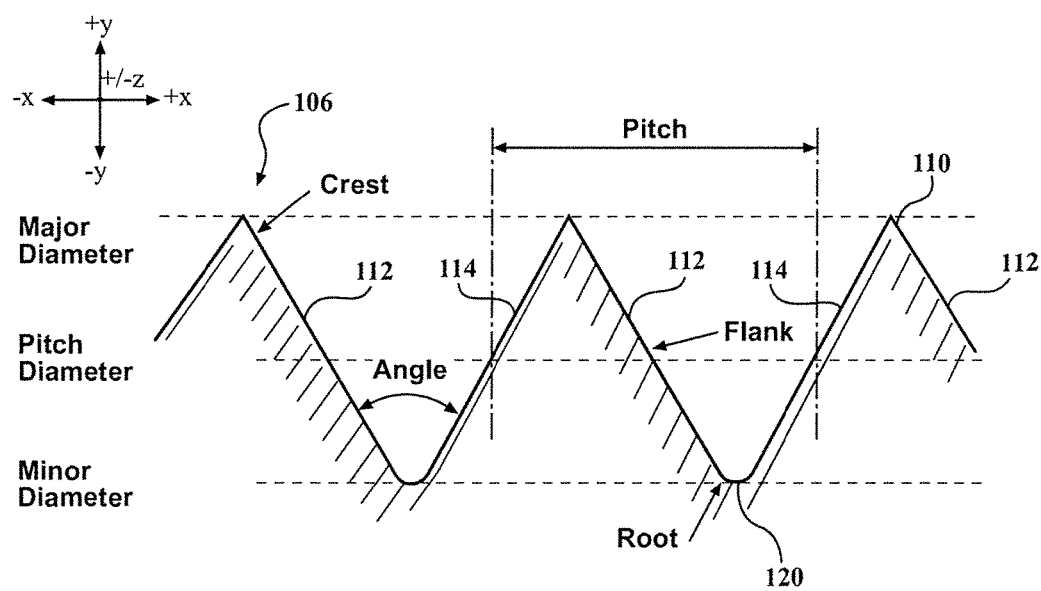
FIG. 2 schematically depicts a longitudinal cross section of a screw.

Referring to FIGS. 1 and 2, a perspective view of a self-locking screw 10 is shown in FIG. 1 and a schematic depiction of a longitudinal (along the length of the self-locking screw 10) cross section along a distal portion 102 of the self-locking screw 10 is shown in FIG. 2. The self-locking screw 10 has a head 104, the distal portion 102, and a shaft 100 extending between the head 104 and the distal portion 102. The shaft 100 includes a thread 106 with a plurality of turns 103 so as to define a root 120. A raised root 130 extends over the root 120 along at least a subset of turns proximal to the head 104. In embodiments, the raised root 130 extends over the root 120 along four or less turns proximal to the head 104.

With reference now to FIG. 2, a longitudinal cross-sectional view of the distal portion 102 of the self-locking screw 10 shown in FIG. 1 is depicted. The thread 106 is formed from a single ridge with a pair of flanks that extend from a single root in a corkscrew manner. However, for the purposes of the instant application, the cross section of the thread 106 will be described as a plurality of flanks and a plurality of roots defining a continuous root spiraling along the shaft 100. Particularly, the thread 106 is described as a plurality of distal end facing flanks 112 and a plurality of head facing flanks 114. A crest 110 is formed by the intersection of one end facing flank 112 and an adjacent head facing flank 114. The root 120 is located between adjacent distal end facing flanks 112 and head facing flanks 114. A "pitch" of the self-locking screw 10 is the distance along a longitudinal axis of the self-locking screw 10 that is covered by one complete rotation of the self-locking screw 10 (360°). A diameter of the pitch (pitch diameter) is defined by the diameter of a cylindrical surface, axially concentric to the thread, which intersects the thread flanks at equidistant points, when viewed in a cross-sectional plane containing the longitudinal axis of the thread, the distance between these points being exactly one half the pitch distance. A diameter of the root 120 is commonly referred to as a "minor diameter" and a diameter of the crest 110 is commonly referred to as a "major diameter."

Figure 3:
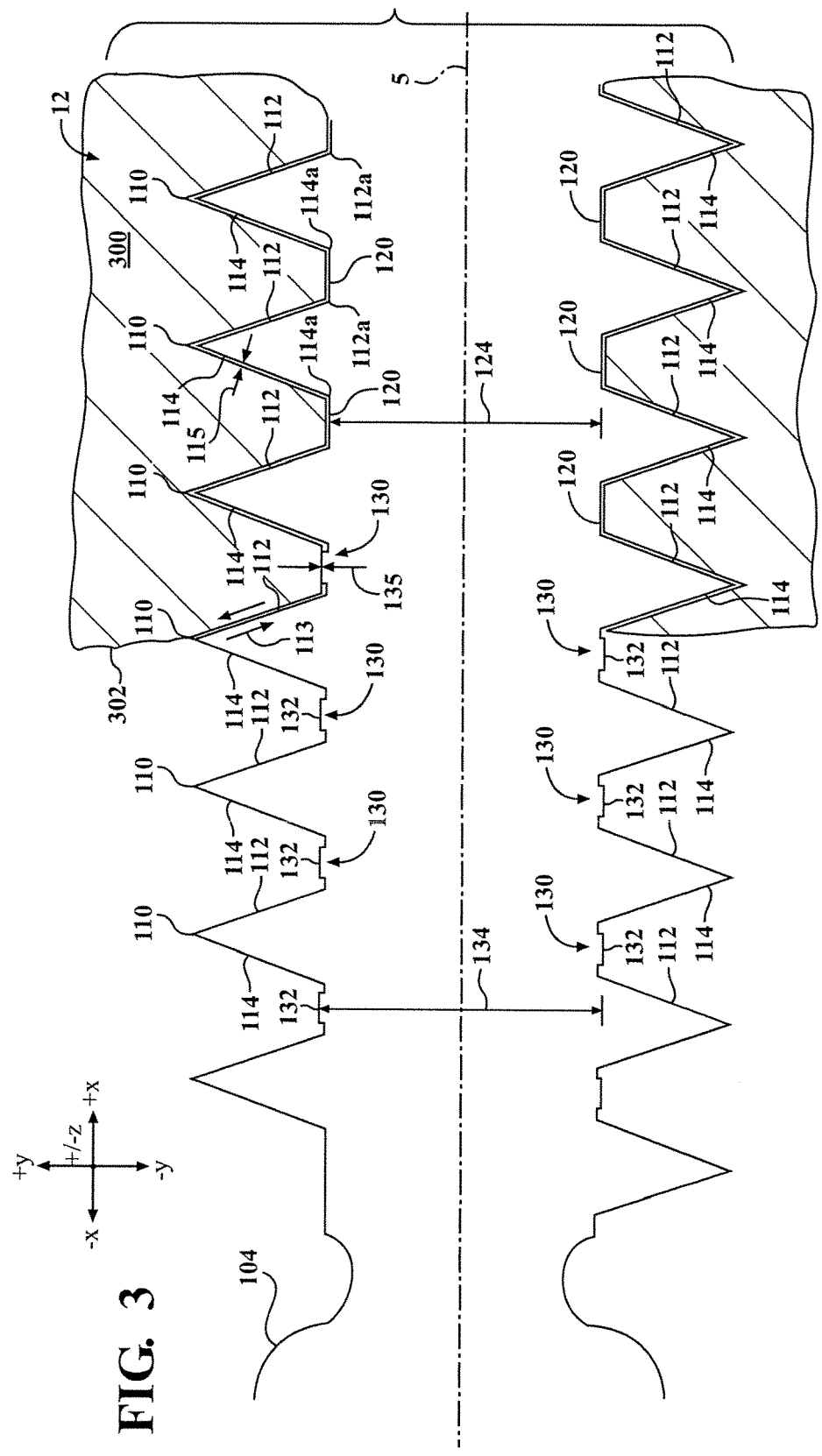
FIG. 3 schematically depicts a longitudinal cross section of a self-locking screw with a raised root according to one or more embodiments shown and described herein.

Referring to FIGS. 1-3, the head facing flanks 114 extend from the root 120 at a corner 114a and the distal end facing flanks 112 extend from the root 120 at a corner 112a. In embodiments, the root 120 has a distance or space between adjacent corners 112a, 114a generally parallel to a screw axis 5. It is appreciated that the root 120 depicted in FIG. 3 has a linear surface between the corners 112a, 114a generally parallel to the screw axis 5. In other embodiments, the root 120 is formed by the intersection of adjacent end facing flanks 112 and head facing flanks 114, i.e. there is no distance or space between adjacent end facing flanks 112 and head facing flanks 114. The self-locking screw 10 depicted in FIG. 3 is shown partially embedded or threaded into a substrate 300 with a distal portion of the self-locking screw 10 being within the substrate 300 and a proximal portion of the self-locking screw 10 being outside of the substrate 300. The self-locking screw 10 includes the raised root 130 with a raised root portion 132 extending over or along the root 120 for at least a subset of turns proximal the head 104.

The root 120 has a first minor diameter 124 and the raised root 130 has a second minor diameter 134 greater than the first minor diameter 124. Screwing of the self-locking screw into the substrate 300 creates sliding frictional forces between the flanks 112, 114 and the substrate 300 in the X-Y plane as illustratively shown by arrows 113 in FIG. 3; compressive forces between the flanks 112, 114 and the substrate 300 in the X-Y plane as illustratively shown by arrows 115; and additional compressive forces between the raised root portion 132 and the substrate 300 in the X-Y plane as illustratively shown by arrows 135. It is appreciated that sliding frictional forces are created between the substrate 300 and the flanks 112, 114, root 120 and raised root 130 in the Y-Z plane and the X-Z plane when the self-locking screw 10 is screwed into the substrate 300. Accordingly, the raised root portion 132 is subjected to additional compressive forces (compared to the root 120 itself) when the self-locking screw 10 is fully inserted or threaded into the substrate 300.

Figure 4:
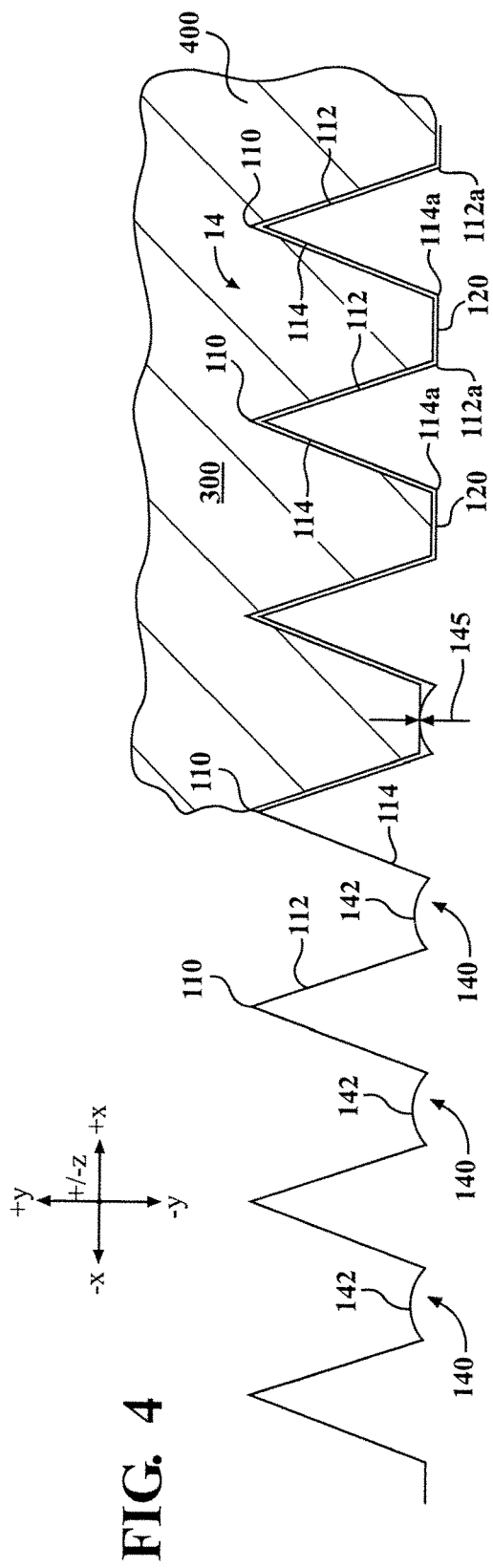
FIG. 4 schematically depicts a longitudinal cross section of a self-locking screw with a raised root according to one or more embodiments shown and described herein.

Referring to FIGS. 1, 2, and 4, a self-locking screw 14 similar to the self-locking screw 10 is depicted, except a raised root 140 with a raised root portion 142 in the form of a dome or arcuate shape is depicted in FIG. 4. The raised root 140 with the raised root portion 142 provides additional compressive forces between the raised root portion 142 and a substrate 400 in the X-Y plane as illustrated by arrows 145 in FIG. 4. It is appreciated that other shapes for the raised root portion can be included such as, without limitation, a triangular shape, a square shape, etc.

Figure 5:
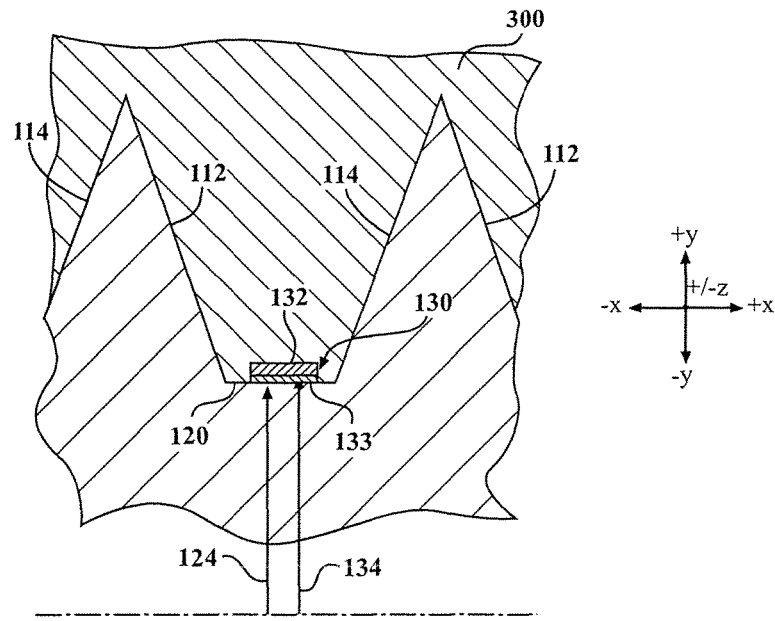
FIG. 5 schematically depicts a longitudinal cross section of a self-locking screw with a raised root according to one or more embodiments disclosed herein.
Figure 6:
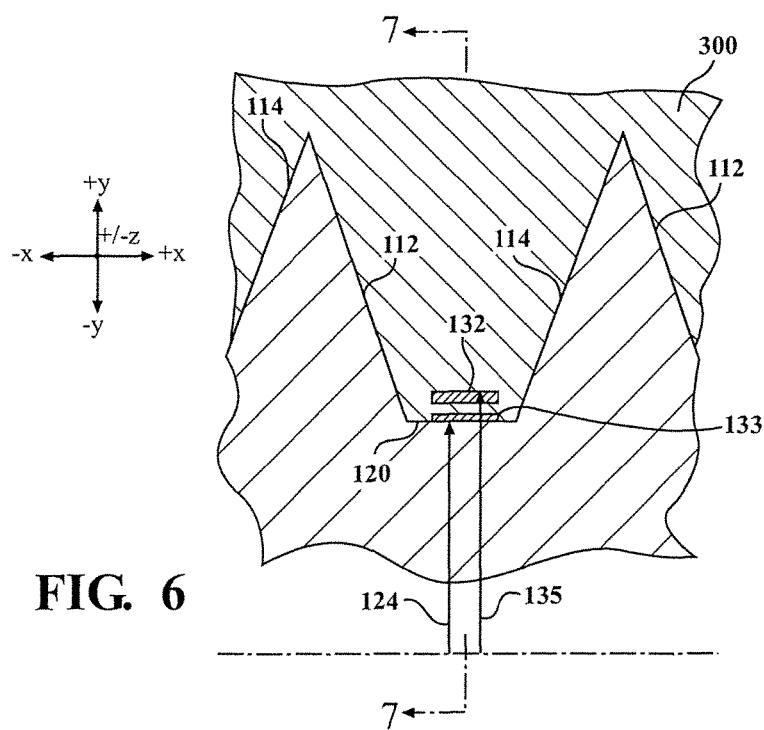
FIG. 6 schematically depicts a longitudinal cross section of a self-locking screw with a raised root detached from a root according to one or more embodiments shown and disclosed herein.
Figure 7:
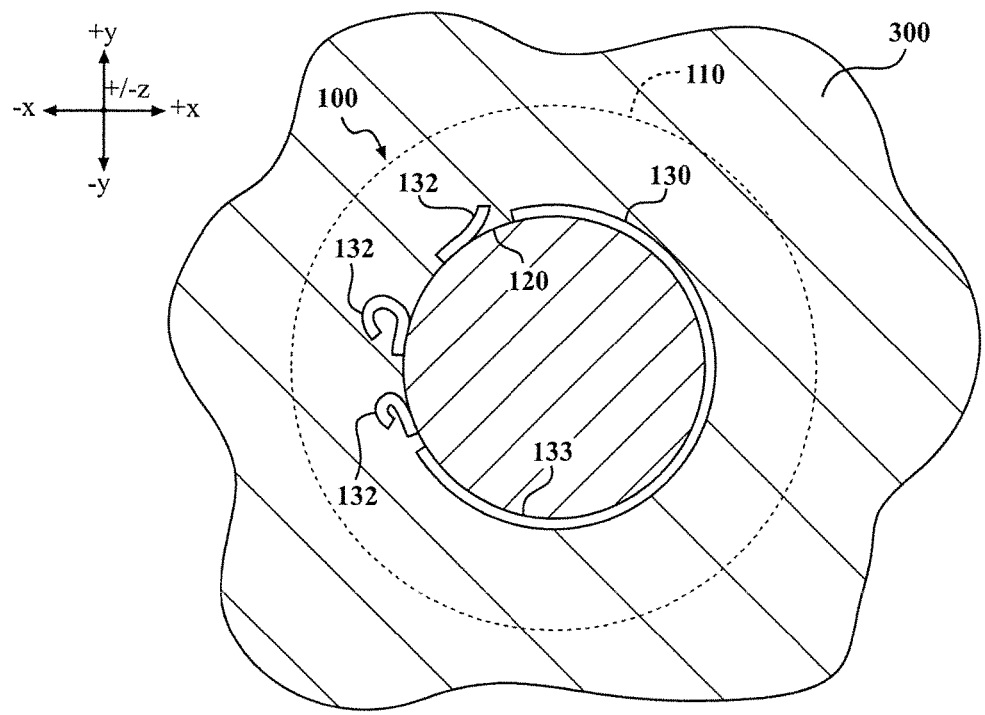
FIG. 7 schematically depicts a radial cross section of a self-locking screw with a raised root detached from a root according to one or more embodiments shown and described herein.

Referring to FIGS. 1-3 and 5-6, one or more embodiments in which the raised root 130 is removably attached to the root 120 are depicted. Particularly, an interface 133 between the raised root portion 132 and the root 120 is shown in FIG. 5. A portion of the raised root portion 132 is removably attached to the root 120 and upon coming into sliding contact with the substrate 300 the raised root portion 132 detaches from the root 120 so as to extend radially into the substrate 300 and find purchase therein, while a portion of the raised root portion remains attached to the root 120, thereby effectively expanding the diameter of the root 120 as described in greater detail below. Detachment of the raised root portion 132 from the root 120 facilitates radial displacement of the raised root portion 132 as depicted in FIG. 6 with the raised root portion 132 detached from the root 120 having a third minor diameter 135 that is greater than the second minor diameter 134 depicted in FIG. 5. In embodiments, the raised root portion 132 can embed within the substrate 300 as depicted in FIG. 7. For example, as the self-locking screw 10 is screwed into the substrate 300 and the turns where the raised root 130 extends over the root 120 come into sliding contact with the substrate 300, the raised root 130 encounters sliding frictional forces from the raised substrate 300. At least a portion of the raised root portion 132 detaches from the root 120 and becomes embedded within the substrate 300. In embodiments, the raised root portion 132 that is detached from the root 120 does not embed within the substrate 300 but binds between the shaft 100 and the substrate 300. For example, the raised root portion 132 may become embedded within a bone substrate, however may not become embedded within an implant substrate and simply bind between the shaft 100 in the implant substrate.

Figure 8:
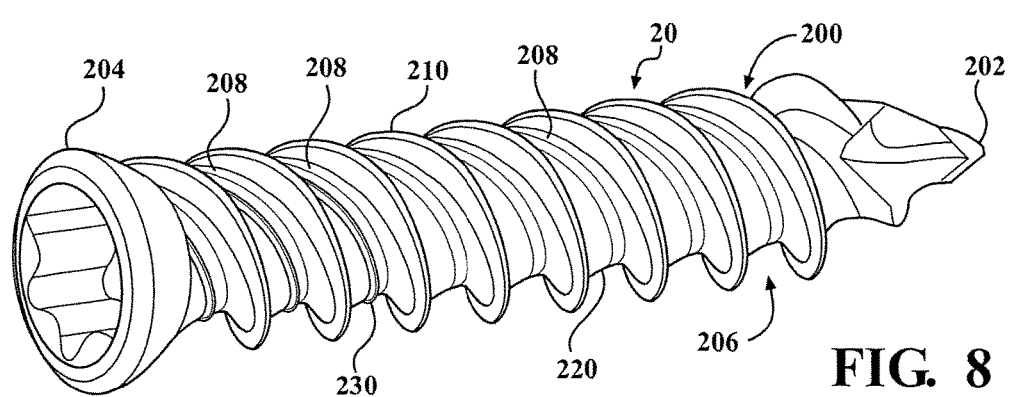
FIG. 8 schematically depicts a perspective view of a self-locking screw according to one or more embodiments shown and described herein.

Referring to FIG. 8, a self-locking screw 20, e.g. an implant screw, is depicted. The self-locking screw 20 has a shaft 200 extending between a distal end 202 and a head 204. The shaft 200 has a thread 206 with a plurality of turns 208 so as to define a root 220. The thread 206 has a crest 210 with flanks (not labeled) as discussed with respect to self-locking screw 10 above. A raised root 230 extends along the root 220 for at least a subset of the turns 208 proximal the head 204. The raised root 230 is releasably attached to the root 220 and detaches from the root 220 when the raised root 230 comes into sliding contact with a substrate when the self-locking screw 120 is screwed into the substrate.

Figure 9:
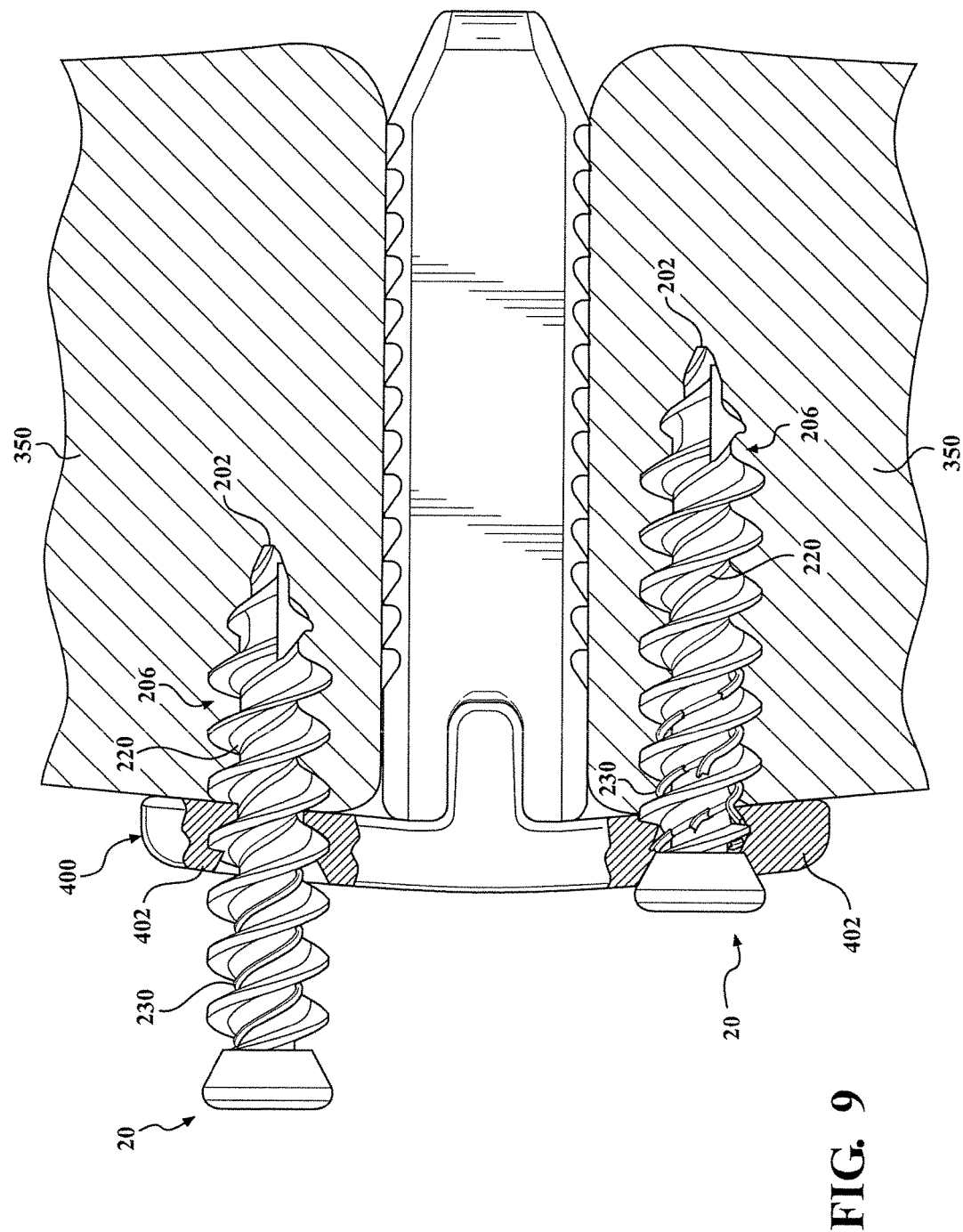
FIG. 9 schematically depicts a pair of self-locking screws, a bone substrate, and an implant substrate according to one or more embodiments shown and described herein.

Referring to FIGS. 8 and 9, a self-locking screw 20, a bone substrate 350, and an implant 400 are depicted. The implant 400 includes an implant substrate 402. One of the self-locking screws 20 is depicted as having been completely screwed into the bone substrate 350 and implant substrate 402. The raised root 230 is depicted as being detached from the root 220 upon coming into sliding contact with the bone substrate 350 and being detached from the root 220 upon coming into sliding contact with the implant substrate 402. Accordingly, as the self-locking screw 20 is screwed into the bone substrate 350 and the raised root 230 comes into sliding contact therewith, a portion of the raised root 230 detaches from the root 220 and becomes embedded within the bone substrate 350 and binds between the shaft 200 and the implant substrate 402. This embedding of a portion of the raised root 230 within the bone substrate 350 and radial expansion of the effective diameter of the root 220 within the bone substrate 350 generates additional compressive forces between the self-locking screw 20 and the bone substrate 350 so as to create a greater binding force relative to prior art screws. Also, binding of the raised root 230 between the shaft 200 and the implant substrate 402 provides the self-locking screw 20 with increased anchoring strength within the implant 400.

In embodiments, the self-locking screw 20 may include a shaft (not labeled) with a taper such that the minor diameter and major diameter at the distal portion 202 of the self-locking screw 20 is less than the minor diameter and major diameter at the proximal portion (proximate to the head 204) of the self-locking screw 20. Also, the raised root 230 may be attached to the root 220 with sufficient strength such that the raised root 230 will not detach from the root 220 upon coming into sliding contact with the bone substrate 350 but will detach from the root 220 upon coming into sliding contact with the implant substrate 402. That is, the sliding frictional forces between the raised root 230 and the bone substrate 350 (when the self-locking screw 20 is being screwed into the bone substrate 350) are not sufficient to detach the raised root 230 from the root 220, but the sliding frictional forces between the raised root 230 and the implant substrate 350 are sufficient to detach the raised root 230 from the root 220. In such embodiments, the taper of the shaft may result in a portion of the raised root 230 extending over the root 220 in the turns proximate the distal portion 202 of the self-locking screw 20 not coming into sliding contact with the implant substrate 402 with sufficient force to detach the raised root 230 from the root 20 as the self-locking screw 20 is being screwed into the bone substrate 350. However, as the proximal end of the self-locking screw 20 is being screwed into the implant substrate 402, the raised root 230 extending over the root in the turns proximate the head 204 of the self-locking screw 200 comes into sliding contact with the substrate 402 with sufficient force to detach the raised root 230 from the root 220. Accordingly, and after the self-locking screw 20 is completely screwed into the bone substrate 350 and implant substrate 402, the raised root 230 located within the bone substrate 350 is not detached from the root 220, but at least a portion of the raised root 230 located within the implant substrate 402 is detached from the root 220 and binds between the shaft of the self-locking screw 20 and the implant substrate 402.

Based on the foregoing, it should now be understood that self-locking screws described herein provide increased anchoring strength when screwed into substrates such as bone substrates, implant substrates, etc. In embodiments, a raised root of a self-locking screw detaches from a root of the self-locking screw and binds between a shaft of the self-locking screw and the bone substrate, implant substrate, etc. In embodiments, the raised root detaches from the root of the self-locking screw and becomes embedded within the bone substrate. The raised root may be made from a same material as the root, or in the alternative, may be made from a different material than the root. For example, the self-locking screw and thus the root may be made from a titanium alloy and the raised root may be made from the same titanium alloy. In embodiments, the raised root may be titanium alloy sponge. The raised root may be an additive manufactured raised root, illustratively including without limitation, a raised root formed by plasma spraying, flame spraying, gas tungsten arc welding, 3D printing, etc. The raised root may be formed from materials illustratively including, but not limited to, polymers, ceramics, etc.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modifications and variations come within the scope of the appended claims and their equivalents.

The invention claimed is:

1. A self-locking screw for binding to a substrate of a surgical site, the self-locking screw comprising:
   a head, a distal portion and a shaft extending between the head and the distal portion;
   the shaft comprising a thread with a plurality of turns so as to define a root;
   a raised root extending over the root, a portion of the raised root integrally formed with the root along at least a subset of the plurality of turns proximal the head, wherein the raised root detaches from the root so as to bind between the shaft and a substrate when the subset of the plurality of turns proximal the head is screwed into the substrate.

2. The self-locking screw of claim 1, wherein the root has a first minor diameter, and the raised root has a second minor diameter greater than the first minor diameter.

3. The self-locking screw of claim 1, further comprising an interface between the root and the raised root, the raised root disengaging from the root at the interface so as to facilitate radial displacement of the raised root and binding of the raised root between the root and the substrate.

4. The self-locking screw of claim 1, wherein the raised root is formed from the same material as the root.

5. The self-locking screw of claim 4, wherein the root and the raised root are formed from a titanium alloy.

6. The self-locking screw of claim 1, wherein the raised root is formed from a titanium alloy sponge.

7. The self-locking screw of claim 1, wherein the raised root is formed from a different material than the root.

8. The self-locking screw of claim 7, wherein the raised root is formed from a material selected from the group consisting of a polymer, an alloy and a ceramic.

9. The self-locking screw of claim 1, wherein the raised root is an additive manufactured raised root.

10. The self-locking screw of claim 1, wherein the substrate is a bone substrate, and the raised root detaches from the root so as to embed within the bone substrate when the shaft is screwed into and the raised root comes into sliding contact with the bone substrate.

11. The self-locking screw of claim 1, wherein the substrate is an implant substrate, and the raised root detaches from the root so as to bind between the root and the implant substrate when the shaft is screwed into the implant substrate and the raised root comes into sliding contact with the implant substrate.

12. The self-locking screw of claim 1, wherein the substrate is a bone substrate and an implant substrate, and the raised root fails to detach from the root when the shaft is screwed into the bone substrate and the raised root comes into sliding contact with the bone substrate, and the raised root detaches from the root and binds between the root and the implant substrate when the shaft is screwed into the implant substrate and the raised root comes into sliding contact with the implant substrate.

13. The self-locking screw of claim 1, wherein the raised root extends over the root for four or less turns proximal the head.

14. The self-locking screw of claim 1, wherein the root is configured to engage the substrate when the raised root is attached to the root.

15. The self-locking screw of claim 1, wherein the root includes a first portion disposed between the raised root and a first turn of the plurality of turns, and a second portion disposed between the raised root and a second turn of the plurality of turns, and wherein the first portion and the second portion are exposed to the substrate when the raised root is attached to the root.

16. The self-locking screw of claim 1, wherein the plurality of turns includes a first turn and a second turn, and wherein the raised root defines an arcuate surface extending between the first turn and the second turn.

17. The self-locking screw of claim 16, wherein the arcuate surface extends from a first flank of the first turn to a second flank of the second turn.

18. The self-locking screw of claim 1, wherein the plurality of turns includes a first turn and a second turn, the root extending a first distance in a first direction from the first turn to the second turn, the raised root extending over the root a second distance in the first direction between the first turn and the second turn, the second distance being less than the first distance.

19. The self-locking screw of claim 18, wherein the screw includes a longitudinal axis extending in a direction substantially parallel to the first direction.

\* \* \* \* \*